United States Patent [19]

Sircar

[11] Patent Number: 4,599,332
[45] Date of Patent: Jul. 8, 1986

[54] 4,5-DIHYDRO-6-[2-[4-(1H-IMIDAZOL-1-YL)PHENYL]-ETHENYL]-3(2H)-PYRIDAZINONES AND RELATED COMPOUNDS

[75] Inventor: Ila Sircar, Ann Arbor, Mich.

[73] Assignee: Warner-Lambert Company, Morris Plains, N.J.

[21] Appl. No.: 669,323

[22] Filed: Nov. 9, 1984

Related U.S. Application Data

[63] Continuation-in-part of Ser. No. 559,161, Dec. 7, 1983, abandoned.

[51] Int. Cl.$^4$ .................. C07D 403/10; A61K 31/50
[52] U.S. Cl. ..................................... 514/247; 544/238; 544/239
[58] Field of Search ................. 544/238, 239; 424/250; 514/247

[56] References Cited

U.S. PATENT DOCUMENTS 4,353,905 10/1982 Sircar ................................. 424/250
4,507,298 3/1985 Lautenschläger .................. 546/238

FOREIGN PATENT DOCUMENTS 0071059 2/1983 European Pat. Off. .
3212304 10/1983 Fed. Rep. of Germany .

*Primary Examiner*—Nicholas S. Rizzo
*Attorney, Agent, or Firm*—Joan Thierstein

[57] ABSTRACT

4,5-Dihydro-6-[2-[4-(1H-imidazol-1-yl)phenyl]alkylenyl or alkylene-3(2H)-pyridazinones and related compounds and pharmaceutically acceptable acid addition salts thereof are useful as cardiotonic and antihypertensive agents.

The above compounds cause a significant increase in myocardial contractility in the dog and also cause a decrease in blood pressure in the spontaneously hypertensive rat. The compounds are produced by reacting the appropriate γ-oxobutanoic acid with a suitably substituted hydrazine to provide 4,5-dihydro-6-[4-[imidazolylphenyl]-alkenylene or alkylene-3(2H)-pyridazinones which may be oxidized to 6-[4-[imidazolylphenyl]alkenylene or alkylene-3(2H)-pyridazinones.

12 Claims, No Drawings

4,5-DIHYDRO-6-[2-[4-(1H-IMIDAZOL-1-YL)PHENYL]-ETHENYL]-3(2H)-PYRIDAZINONES AND RELATED COMPOUNDS

CROSS-REFERENCE TO RELATED APPLICATION

This application is a continuation-in-part of U.S. Ser. No. 559,161 of Dec. 7, 1983, now abandoned.

BACKGROUND OF THE INVENTION

6-Pyridyl-vinyl-pyridazine-3(2H)-one and the 4,5-dihydro compound have been described as having cardiotonic and/or antihypertensive activity in European Patent Application 81,906.

SUMMARY OF THE INVENTION

The present invention relates to 4,5-dihydro-6-[2-[4-(1H-imidazol-1-yl)phenyl]alkylenyl and alkylene-3(2H)-pyridazinones and their derivative compounds which have valuable pharmacological properties and in particular cardiotonic, antihypertensive, and antithrombotic activities.

Accordingly, the present invention is a compound of the formula

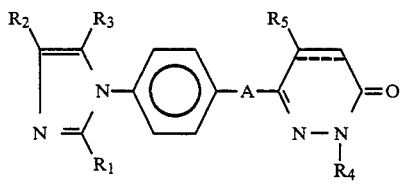

wherein ≡≡≡ signifies a single or double bond; $R_1$, $R_2$, and $R_3$ are each independently hydrogen, lower alkyl, hydroxy lower alkyl or $R_2$ and $R_3$ when taken together may form a ring containing five to seven carbon atoms or a benzene ring; $R_4$ and $R_5$ are each independently hydrogen or lower alkyl; A is alkylene of one to four carbon atoms or alkenylene of two to four carbon atoms, or a pharmaceutically acceptable acid addition salt thereof; as well as a pharmaceutical composition comprising an effective amount of a compound of formula I together with a pharmaceutically acceptable carrier; a process for preparing the compound of formula I; a method for increasing cardiac contractility in a mammal in need thereof which comprises administering to said mammal an effective amount of a pharmaceutical composition containing a compound of formula I, and a method of lowering blood pressure in a mammal suffering from hypertension and the prophylaxis and therapy of thromboembolistic diseases which comprises administering to said mammal an effective amount of a pharmaceutical composition containing a compound of formula I.

DETAILED DESCRIPTION

The term "alkylene of one to four carbon atoms" refers to a straight or branched hydrocarbon chain bonded at each end to other groups and is, for example, ethylene, 1-methylethylene, propylene, butylene, 1-methylpropylene, 2-methylpropylene, or 1,1-dimethylethylene.

The term "alkenylene of two to four carbon atoms" refers to a straight or branched hydrocarbon chain containing a double bond and bonded to other groups at each end and is, for example, ethenylene, allylene, 1-methylethenylene, 3-methyl-1-propenylene, 1-butenylene, 2-butenylene, 2-methyl-1-propenylene, and the like.

The compounds of formula I are useful both in the free base form and in the form of acid addition salts. Both forms are within the scope of the invention. The acid addition salts are a more convenient form for use; and in practice, use of the salt form amounts to use of the base form. In practicing the invention, it was found convenient to form the sulfate, phosphate, or methanesulfonate salts. However, other appropriate pharmaceutically acceptable salts within the scope of the invention are those derived from mineral acids such as hydrochloric acid and sulfamic acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compound of formula I where $R_4$ is hydrogen and ≡≡≡ signifies a double bond may exist in tautomeric forms, that is, as 6-[2-[4-(1H-imidazol-1-yl)phenyl]alkylenyl or alkylene-3(2H)-pyridazinones of formula II or as 6-[2-[4-(1H-imidazol-1-yl)phenyl]alkylenyl or alkylene-3-pyridazinols of formula IIA as follows:

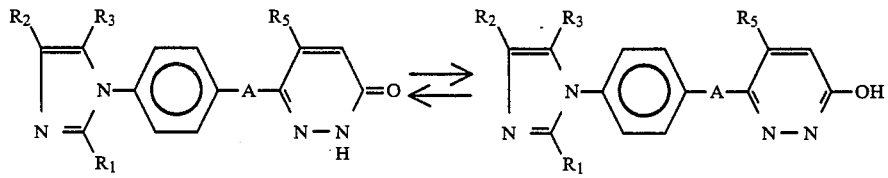

II          IIA

A preferred embodiment of the present invention is a compound of the formula I, wherein ≡≡≡ represents a single or double bond; $R_1$, $R_2$, $R_3$, $R_4$, and $R_5$ are each independently hydrogen or methyl, and A is alkenylene of two to four carbon atoms, or alkylene of one to four carbon atoms, or a pharmaceutically acceptable acid addition salt thereof.

Another preferred embodiment is a compound of formula I, wherein ══ is a single or double bond; $R_1$, $R_2$, $R_3$, $R_4$, and $R_5$ are each independently hydrogen or methyl, and A is methylene, ethylene, propylene, or particularly, vinylene.

A particular embodiment of the present invention is 4,5-dihydro-6-[2-[4-(1H-imidazol-1-yl)phenyl]ethenyl]-3(2H)-pyridazinone.

Another preferred embodiment of the present invention is 4,5-dihydro-6-[2-[4-(1H-imidazol-1-yl)phenyl]ethenyl]-5-methyl-3(2H)-pyridazinone.

The compounds of formula I may be prepared by a process which comprises reacting a γ-oxobutanoic acid of the formula

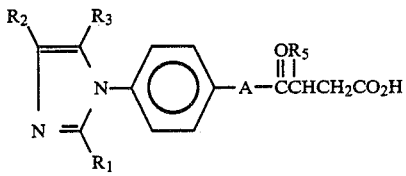

wherein A, $R_1$, $R_2$, $R_3$, and $R_5$ have been defined above, with a $R_4$-hydrazine or hydrate thereof, in which $R_4$ is defined above, in an alcohol solvent or acid/alcohol mixture, such as ethanol or ethanol/acetic acid, at elevated temperatures, such as from 50°–100° C., to produce a compound of the formula

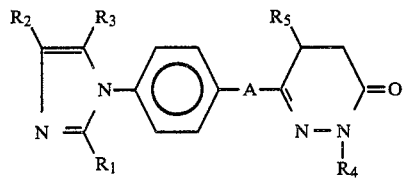

which, when desired, is converted to a compound of the formula

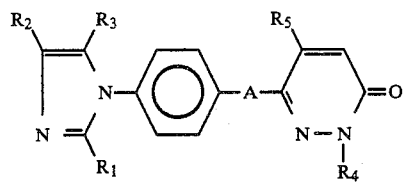

with an oxidizing agent such as manganese dioxide or m-nitrobenzenesulfonic acid according to a procedure described by W. V. Curran and A. Ross in *J. Med. Chem.*, 17, 273 (1974).

The γ-oxobutanoic acids used as starting materials are known or, if new, may be prepared by known means, for example by condensing the appropriate 4-(1H-imidazol-1-yl)phenylcarboxaldehyde with an oxobutanoic acid as described in European Patent Applications 81,906 and 85,227.

The following schematic diagram illustrates by way of example the preparation of a compound of formula I, wherein A is ethenylene and/or ethylene. The ethylene compound may be obtained by catalytic hydrogenation of the vinylene compound. Palladium on carbon (10%) is preferably used in an alcohol solvent such as ethanol.

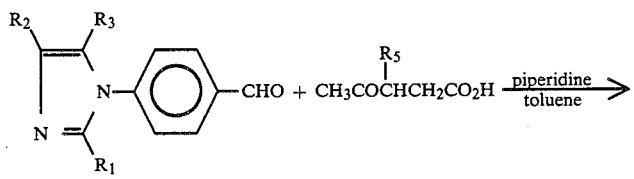

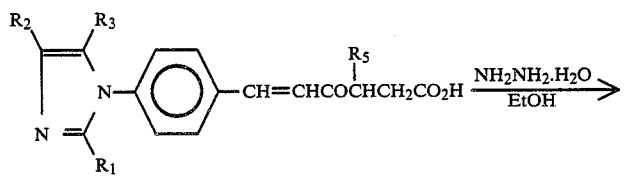

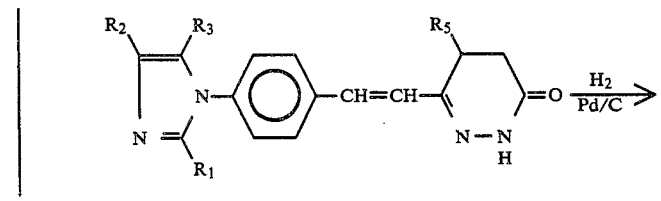

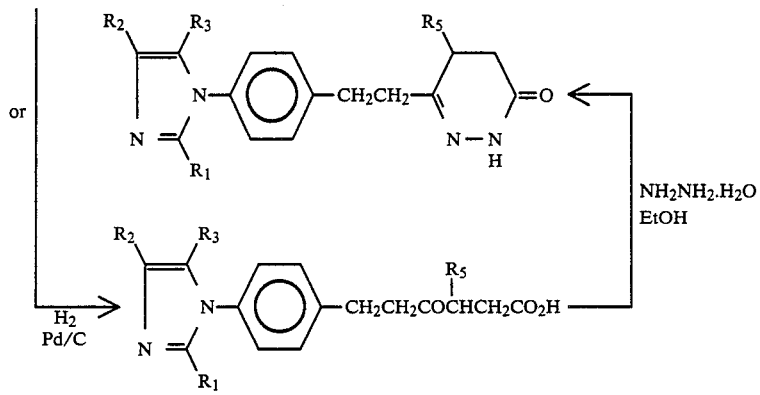

The usefulness of the compounds of the present invention as cardiotonic agents is demonstrated by their effectiveness in standard pharmacological test procedures, for example, in causing a significant increase in the myocardial contractility in the pentobarbital-anesthetized dog with low or minimal changes in heart rate and blood pressure. This test procedure is described in the following paragraphs.

Test For In Vivo Myocardial Inotropic Activity In Anesthetized Dog

This screen consists of determining the effects of increasing intravenous doses of compound on myocardial contractility (dP/dt max of left ventricular blood pressure), heart rate, and aortic blood pressure of the pentobarbital-anesthetized dog.

Methods

Adult mongrel dogs of either sex are anesthetized with pentobarbital, 35 mg/kg, IV, and are subsequently maintained under anesthesia with a continuous infusion of pentobarbital, 3.5 mg/kg/hour. The trachea is intubated but the animals are permitted to breathe spontaneously. A cannula is inserted into the femoral vein for administrating test agents. A Millar catheter tip pressure transducer or a fluid filled catheter is inserted into the ascending aorta via the femoral artery for measuring aortic blood pressure. A Millar catheter tip pressure transducer is passed into the left ventricle via the left carotid artery for measuring left ventricular blood pressure. Needle electrodes are placed subcutaneously for recording a lead II electrocardiogram (ECG).

Left ventricular and aortic blood pressures are recorded on a strip chart recorder. Heart rate, using a biotachometer triggered from the R wave of the ECG, and the first derivative of left ventricular blood pressure (dP/dt), obtained with a differentiator amplifier coupled to the corresponding pressure amplifier, are also recorded. A period of at least 30 minutes is utilized to obtain control data prior to administration of test compound.

Depending on solubility, the compounds are dissolved in 0.9% saline solution or in dilute HCl or NaOH (0.1 or 1.0N) and are diluted to volume with normal saline. Ethanol or dimethylacetamide can be used as solvents if adequate dilutions can be made. Appropriate vehicle controls are administered when needed.

Each dose of the test compound is administered in a volume of 0.1 ml/kg over a period of one minute.

When tested by the above-described Anesthetized Dog Procedure, the compounds of the present invention when administered intravenously at a rate of about 0.01 to 0.31 mg/kg/min caused dose related significant increases in cardiac contractility with only low or minimal changes in heart rate and moderate reduction in blood pressure. Thus the compounds of the present invention are also useful as antihypertensive agents.

Test Result of 4,5-Dihydro-6-[2-[4-(1H—imidazol-1-yl)-phenyl]ethenyl-3(2H)—pyridazinone Using Anesthetized Dog Procedure

| Compound | Dose mg/kg | Percent Change | | |
|---|---|---|---|---|
| | | Myocardial Contractility | Heart Rate | Blood Pressure |
| 1a | .001 | 6 | 4 | 2 |
| | .003 | 9 | 2 | 3 |
| | .01 | 29 | 1 | −2 |
| | .03 | 90 | 0 | −7.5 |
| | 0.1 | 175 | 10 | −13.5 |

Accordingly, the present invention also includes a pharmaceutical composition for increasing cardiac contractility and/or treating hypertension comprising an effective amount of a compound of the formula I as defined above together with a pharmaceutically acceptable carrier.

The present invention further includes a method for increasing cardiac contractility and/or treating hypertension in mammals suffering therefrom comprising administering to such mammals either orally or parenterally a corresponding pharmaceutical composition containing a compound of the formula I as defined above in appropriate unit dosage form.

The usefulness of the compounds of the present invention as antithrombotic agents is demonstrated by their effectiveness in inhibiting human platelet aggregation in standard in vitro platelet aggregation tests using human platelet-rich plasma.

Source of Platelets

Blood is collected from volunteers who have not injested aspirin or other nonsteroidal antiinflammatory drugs within the preceding two weeks and have not eaten within nine hours before blood draw. Blood is collected in 4.5 ml portions in Vacutainer Number 6462S silicone-coated tubes containing 0.5 ml of 3.8% trisodium citrate. Usually six portions of 4.5 ml are drawn from each volunteer. The blood collected from three or four volunteers is pooled prior to centrifugation. The pooled blood is put in 50 ml polyethylene tubes and centrifuged at 80 xg (ca 600 rpm) in an International Model K centrifuge with number 240 rotor for 20 minutes as room temperature. A portion (approximately two-thirds) of the supernatant platelet-rich plasma (PRP) is removed and set aside, and the remaining blood sample is recentrifuged at 1400 xg (ca 2800 rpm) for 15 minutes to prepare platelet-poor plasma (PPP). The platelet content of the PRP is determined with a Coulter Thrombocounter. The PRP is adjusted to a count of 250,000 platelets per microliter using the PPP.

Preparation of Drug Solutions

Test drugs are dissolved in small amounts of dimethyl sulfoxide (DMSO) followed by dilution with saline (final concentration of DMSO is 1%). Other lower concentrations are prepared by serial dilution in saline.

Technique of Aggregation Measurement

Platelet-rich plasma adjusted to 250,000 platelets per microliter is distributed in 0.36 ml aliquots into silicone-coated cuvettes of 0.312 inch diameter. Addition of drug solution or saline (0.02 ml) is followed by addition of aggregating agents (ADP or collagen suspension, 0.02 ml). Extent of aggregation (ADP stimulus) or rate of aggregation (collagen stimulus) is determined using the Payton Scientific Dual Channel Aggregation Module, Model 300B. Appropriate concentrations of aggregating agents are determined by an initial brief titration.

Calculations

ADP-Induced Aggregation

The height in millimeters of aggregation curves for control (no drug addition, saline only) aggregations are compared with the heights of curves obtained after drug addition at various appropriate concentrations. Heights after drug addition are finally expressed as "percent of control" values. These values are plotted versus drug concentration on semilog paper. Estimates of $IC_{50}$ values can then be made from the resulting curves.

Collagen-Induced Aggregation

The major slopes (i.e., the slope of the longest straight line portion) of collagen-induced aggregation curves are determined and compared to the slopes obtained for control aggregation curves (saline and aggregating agent only added). Values obtained are expressed as "percent of control" values. These values are plotted versus drug concentration on semilog paper. Estimates of $IC_{50}$ values are made from the resulting curves.

When tested by the above procedure, 4,5-dihydro-6-[2-[4-(1H-imidazol-1-yl)phenyl]ethenyl-5-methyl-3-(2H)-piperidazinone had a very potent $IC_{50}$ of $7 \times 10^{10}M$ against collagen-induced aggregation and had an $IC_{50}$ of $1 \times 10^7 M$ against ADP-stimulated aggregation.

Accordingly, the present invention also includes a method for treating thrombosis in mammals suffering therefrom comprising administering to such mammals either orally or parenterally a corresponding pharmaceutical composition containing a compound of the formula I as defined above in "Appropriate Unit Dosage Form."

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.03 to 100 mg/kg of body weight per day or preferably 0.1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

4,5-Dihydro-6-[2-[4-(1H-imidazol-1-yl)phenyl]-ethenyl]-3(2H)-pyridazinone (1a)

A solution of 2 g of (E)-6-[4-(1H-imidazol-1-yl)phenyl]-4-oxo-5-hexenoic acid in 60 ml of ethanol containing 0.5 g of 80% hydrazine hydrate is heated to reflux for three hours. The solution is concentrated to a small volume (ca 10 ml) and filtered. The residue is crystallized from THF/methanol to give 0.6 g of the 4,5-dihydro-pyridazinone, mp 230°–231° C.

Anal. Calcd for $C_{15}H_{14}N_4O$: C, 67.65; H, 5.30; N, 21.04; Found: C, 67.50; H, 5.32; N, 21.00.

Similarly by following the procedure in Example 1, the following compounds are obtained: 4,5-Dihydro-6-[2-[4-[4,5,6,7-tetrahydro-1H-benzimidazol-1-yl)phenyl]ethenyl]-3(2H)-pyridazinone, mp 234°–235° C. (1b).

Anal. Calcd for $C_{19}H_{20}N_4O$: C, 71.22; H, 6.29; N, 17.49; Found: C, 71.06; H, 6.16; N, 17.19.

4,5-Dihydro-6-[2-[4-(1H-imidazol-1-yl)phenyl]ethenyl-5-methyl-3(2H)-pyridazinone, mp 183°–184° C. (1c).

Anal. Calcd for $C_{16}H_{16}N_4O$: C, 68.55; H, 5.75; N, 19.79; Found: C, 68.24; H, 5.76; N, 19.74.

EXAMPLE 2

4,5-Dihydro-6-[2-[4-(1H-imidazol-1-yl)phenyl]-ethyl]-3(2H)-pyridazinone

A solution of 2.6 g of 4,5-dihydro-6-[2-[4-(1H-imidazol-1-yl)phenyl]ethenyl]-3(2H)-pyridazinone in 100 ml of 2-methoxyethanol containing 0.5 g of 10% Pd/C is shaken under hydrogen atmosphere for 13 hours. The catalyst is filtered, the filtrate is evaporated to dryness, and the residue is crystallized from ethanol to give 2 g of the above product, mp 195°–196° C.

Anal. Calcd for $C_{15}H_{16}N_4O$: C, 67.14; H, 6.01; N, 20.88; Found: C, 66.96; H, 6.18; N, 20.85.

Preparative Example (E)-6-[4-(1H-imidazol-1-yl)phenyl]-4-oxo-5-hexenoic acid A mixture of 3.4 g (0.02 mol) of 1-[4-(1H-imidazol-1-yl)-phenyl]carboxaldehyde [prepared according to the general methods of L. M. Sitkina and A. M. Simonov, *Khim. Geterotsikl. Soedin. Akad. Nauk. Laliv. SSR*, 143 (1966)-*Chem. Abstr.* 65, 13686 (1966)] and 2.3 g (0.02 mol) of levulinic acid in 100 ml of toluene containing 0.5 ml of piperidine is refluxed for four hours with continuous removal of water. The reaction mixture is cooled, filtered, and the residue is washed with methanol to give 3 g of the acid, mp 264°–265° C.

Similarly, by substituting 1-[4-(4,5,6,7-tetrahydro-1H-benzimidazol-1-yl)phenyl]carboxaldehyde in place of 1-[4-(1H-imidazol-1-yl)-phenyl]carboxaldehyde in the above Example, a sample of (E)-6-[4-(4,5,6,7-tetrahydro-1H-benzimidazol-1-yl)phenyl]-4-oxo-5-hexenoic acid is obtained.

Similarly, by substituting methyl levulinic acid [prepared according to the procedure of R. P. Evstigneeva et al., *2h. Obshch. Khim.* 34, 10, 3308–12 (1964)-*Chem. Abs.* 62, 3949h (1965)] in place of levulinic acid in the above Example, a sample of (E)-6-[4-(1H-imidazol-1-yl)phenyl]-3-methyl-4-oxo-5-hexenoic acid is obtained.

I claim:

1. A compound of the formula

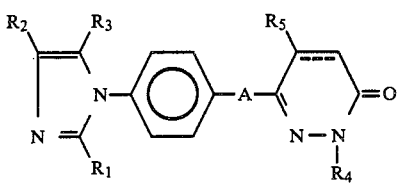

wherein ===== is a single or double bond; $R_1$, $R_2$ and $R_3$ are each independently hydrogen, lower alkyl, hydroxyl lower alkyl or $R_2$ and $R_3$ when taken together may form a ring containing five to seven carbon atoms or a benzene ring; $R_4$ and $R_5$ are each independently hydrogen or lower alkyl; A is alkylene of one to four carbon atoms or alkenylene of two to four carbon atoms, or a pharmaceutically acceptable acid addition salt thereof.

2. A compound as claimed in claim 1, wherein $R_1$, $R_2$, $R_3$, $R_4$, and $R_5$ are each independently hydrogen or methyl.

3. A compound as claimed in claim 2, wherein A is vinylene.

4. A compound as claimed in claim 3, and being 4,5-dihydro-6-[2-[4-(1H-imidazol-1-yl)phenyl]ethenyl]-3(2H)-pyridazinone.

5. A compound as claimed in claim 1, and being 4,5-dihydro-6-[2-[4-(4,5,6,7-tetrahydro-1H-benzimidazol-1-yl)phenyl]ethenyl]-3(2H)-pyridazinone.

6. A compound as claimed in claim 3, and being 4,5-dihydro-6-[2-[4-(1H-imidazol-1-yl)phenyl]ethenyl-5-methyl-3(2H)-pyridazinone.

7. A compound as claimed in claim 1, and being 4,5-dihydro-6-[2-[4-(1H-imidazol-1-yl)phenyl]-ethyl]-3(2H)pyridazinone.

8. A pharmaceutical composition comprising an effective amount for treating a mammal in need of the effect comprising increased cardiac contractility, lower blood pressure or antithrombosis with a compound as claimed in claim 1 together with a pharmaceutically acceptable carrier.

9. A method for increasing cardiac contractility in mammals in need thereof which comprises administering to such mammal an effective amount of a composition as claimed in claim 8.

10. A method for lowering blood pressure in a mammal suffering from hypertension which comprises administering to said mammal an effective amount of a composition as claimed in claim 8.

11. A method for treating thrombosis in a mammal suffering therefrom which comprises administering to said mammal an effective amount of a composition as claimed in claim 8.

12. A process for the preparation of a compound as claimed in claim 1 which comprises reacting a compound of the formula

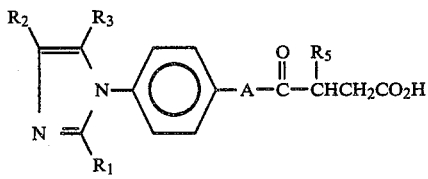

with an $R_4$-hydrazine or hydrate thereof in an alcohol or alcohol/acid media at elevated temperatures, and, if desired, converting the resulting compound of formula I in claim 1 wherein ===== is a single bond to a corresponding compound wherein ===== is a double bond with an oxidizing agent, and, if desired, converting a resulting free base of a compound of the formula I to a corresponding pharmaceutically acceptable acid addition salt.

* * * * *